United States Patent [19]

Padia et al.

[11] Patent Number: 5,360,916
[45] Date of Patent: Nov. 1, 1994

[54] TWO STAGE BUTANE HALEIC ANHYDRIDE PROCESS

[75] Inventors: Ashok S. Padia, Glenrock, N.J.; Gaylon T. Click, Wilson County, Tex.

[73] Assignee: Scientific Design Company, Inc., Little Ferry, N.J.

[21] Appl. No.: 152,088

[22] Filed: Nov. 15, 1993

Related U.S. Application Data

[63] Continuation of Ser. No. 681,046, Apr. 5, 1991, abandoned.

[51] Int. Cl.$^5$ ............................................. C07D 307/60
[52] U.S. Cl. ..................................... 549/259; 549/260
[58] Field of Search ............................... 549/259, 260

[56] References Cited

U.S. PATENT DOCUMENTS

| | | | |
|---|---|---|---|
| 2,294,130 | 8/1942 | Porter | 549/260 |
| 4,044,027 | 8/1977 | Anderson et al. | 549/259 |
| 4,116,983 | 9/1978 | Schmidt | 549/257 |

OTHER PUBLICATIONS

Jost, Explosion and Combustion Processes in Gases, McGraw-Hill, N.Y., (1946) pp. 234, 437–440 and 444–454.

Arnold, III et al., Applied Catalysis, vol. 41, pp. 225–239 (1988).

*Primary Examiner*—Bernard Dentz
*Attorney, Agent, or Firm*—Kenneth H. Johnson

[57] ABSTRACT

Butane is oxidized with molecular oxygen in a dilute state by bringing a mixture of vaporized butane and air of controlled butane content into the presence of a contact vanadium-phosphorus-oxygen catalyst in a first oxidation zone under controlled pressure and temperature conditions, cooling the gaseous effluent from the first oxidation zone to a temperature in the range of 50° to 300° C., introducing a controlled amount of butane into the cooled gaseous effluent from the first oxidation zone, introducing said cooled butane-enriched stream into the second oxidation zone, and bringing the thus butane-enriched mixture into contact with a vanadium-phosphorus-oxygen catalyst disposed in the second zone.

26 Claims, No Drawings

TWO STAGE BUTANE HALEIC ANHYDRIDE PROCESS

This application is a continuation of application Ser. No. 07/681,046, filed Apr. 5, 1991, now abandoned.

FIELD OF THE INVENTION

The present invention relates to the catalytic oxidation of $C_4$-$C_{10}$ hydrocarbons and is more particularly concerned with the preparation maleic anhydride (MAN) by such oxidation of butane.

RELATED ART

Maleic Anhydride is currently produced by the oxidation of hydrocarbons such as benzene, butene, butadiene-1,3 or butane. Generally, maleic anhydride is obtained by oxidizing the hydrocarbon feed at a high temperature and over a suitable catalyst to produce a gaseous effluent of maleic anhydride together with impurities. The gaseous effluent is cooled and scrubbed with water to produce a crude solution of maleic acid. The aqueous solution of maleic acid is then fed to a dehydration-distillation column in which the maleic acid is dehydrated by contacting with a volatile water insoluble entraining or azeotroping agent such as xylene which does not undergo chemical reaction in the system. The water and entraining agent are removed as overhead vapors and maleic anhydride is removed as bottoms. The maleic anhydride is then further purified, as required.

The production of maleic anhydride by the partial oxidation of butane in a vapor-phase system using a contact catalyst, which serves to moderate the selectivity of the reaction, involves a well-known reaction and has been practiced commercially for many years. Thus, a typical commercial process involves passing a mixture of air and butane in vapor form containing about 0.5 to 4 and preferably about 1 to 2 mole percent of butane over a catalyst disposed in tubes arranged in a reactor vessel. The tubes are surrounded by a heat transfer liquid bath, e.g. a salt. Following the reaction, the hot gaseous effluent from the converter is suitably treated to recover the maleic anhydride. The gaseous product stream is passed to a scrubbing zone, where it is contacted with a scrubbing liquid, usually water, so that the maleic anhydride entrained in the gaseous stream is extracted by the water, forming an aqueous maleic acid solution. The maleic acid solution is then sent to a dehydration zone for removal of water and conversion of the maleic acid to maleic anhydride. The dehydration treatment may be carried out in the presence of an organic water-entraining agent, such as xylene or toluene, which, forming an azeotrope with the water, aids in its removal. The maleic acid solution is heated in the dehydration zone to an elevated temperature, and the water and azeotroping agent are vaporized away from the maleic anhydride which is produced. The crude maleic anhydride thus recovered may be further treated to produce substantially pure product.

These processes for the oxidation of hydrocarbons to maleic anhydride, scrubbing of the maleic anhydride to produce an aqueous maleic acid solution and dehydration of the maleic acid solution to form maleic anhydride are known in the art and are described, for example, in Chemical and Engineering News 38, (28),40, 1960; Encyclopedia of Polymer Science (1964); Kirk and Othmer Encyclopedia of Chemical Technology, 2nd edition, Vol. 12,828, Interscience (1967); U.S. Pat. No. 2,683,110 and U.S. Pat. No. 3,094,539.

Primary goals of the commercial production of maleic anhydride are (1) to achieve the maximum yield of product from the butane employed, (2) to increase the productivity of a given commercial unit i.e., to produce the maximum amount of maleic anhydride from a plant of a given size and (3) produce maximum maleic anhydride with minimum use of energy. The use of highly active catalysts makes it possible to increase butane conversion and selectivity to the desired maleic anhydride. The process is nevertheless limited since the mixtures of oxygen-containing gas and butane must be relatively dilute with respect to butane in order to lessen flammability problems. This dilute solution also causes the cost of compressing air to be high. A somewhat similar situation exists in connection with the catalytic oxidation of benzene to produce maleic anhydride. In this connection, it has been proposed in U.S. Pat. No. 4,116,983 to carry out the oxidation in a series of catalyst chambers with the effluent from one chamber being passed into the inlet of the next succeeding chamber until the hydrocarbon has been substantially exhausted. According to the patent, benzene is oxidized with molecular oxygen in a first reactor in the presence of a contact catalyst comprising vanadium and molybdenum and the gaseous effluent from the first reactor is passed into a second reactor substantially at a temperature at least as great as the temperature in the first oxidation zone while introducing a controlled amount of benzene, generally 0.8 to 1.8 mole percent, into the gaseous effluent from the first reactor prior to its introduction into the second reactor, and bringing the benzene-enriched mixture into contact with a catalyst comprising vanadium and molybdenum disposed in the second reactor. According to the patent in the benzene process cooling of the effluent from the first stage reactor is preferably held to a minimum and is not essential from a process standpoint.

It has been found that the two reactor process as disclosed in the patent is not suitable for the partial oxidation of butane. The injection of the additional butane into the hot gaseous effluent stream from the first reactor will result in a phenomenon known as "cold flame" reaction, in which butane reacts with oxygen without a catalyst to produce a polyglot mixture of oxidation products, which both reduce the yield of MAN and cause problems in purifying the MAN.

SUMMARY OF TEE INVENTION

In accordance with the present invention, butane is oxidized with molecular oxygen in a dilute state by bringing a mixture of vaporized butane and air of controlled butane content into the presence of a contact vanadium-phosphorus-oxygen catalyst in a first oxidation zone under controlled pressure and temperature conditions, cooling the gaseous effluent from the first oxidation zone to a temperature in the range of 50° to 300° C., introducing a controlled amount of butane into the cooled gaseous effluent from the first oxidation zone, introducing said cooled butane enriched stream into the second oxidation zone, and bringing the thus butane-enriched mixture into contact with a vanadium-phosphorus-oxygen catalyst disposed in the second zone.

The temperature range of the cooled gaseous effluent from the first reaction zone is critical. The cold flame reaction rate is dependent upon several factors, i.e., temperature, butane concentration, residence time etc. At temperatures of below 200° C. the cold flame reaction is not great enough to cause problems in yield or purification when operated in existing maleic anhydride plants. Therefore the upper temperature limit is important. It should be appreciated that the significant aspect of this cold flame reaction is that it occurs below the auto ignition temperature of butane which is about 372° C. and that it proceeds in the absence of the catalyst. If the effluent stream from the first reaction zone is not cooled quickly and particularly before the addition of the make-up butane, then lines, headers, etc., that is, any area not containing the catalyst becomes a cold flame reactor.

DETAILED DESCRIPTION AND PREFERRED EMBODIMENTS

It has been found that, in the case of the oxidation of butane to maleic anhydride, it is necessary to operate under conditions maintained within relatively narrow ranges while using air-butane mixtures containing selected quantities of vaporized butane. The gaseous feed stream to the first oxidation zone normally will contain air and about 0.5 to about 2.5 mole percent hydrocarbons such as n-butane. About 1 to about 2 mole percent of the n-$C_4$ hydrocarbon are satisfactory for optimum yield of product for the process of this invention. Although higher concentrations may be employed, explosive hazards may be encountered. Lower concentrations of $C_4$, less than about one percent, of course, will reduce the total productivity obtained at equivalent flow rates and thus are not normally economically employed.

The butane content to the second reactor is, of course, the sum of the unreacted butane in the effluent from the first reactor plus fresh butane injected into the effluent prior to its introduction into the second reactor. However in the second stage reactor in addition to butane there is present the maleic anhydride product of the first stage reactor, which adversely effects flammability of the mixture such that the preferred upper limit of butane in the second reactor is about 1.8 mole percent, otherwise the concentration of butane in the second stage is the same as in the first stage. No additional oxygen is added to the feed to the second reactor, therefore the oxygen content in the second reactor is lower which reduces the flammability of this stream somewhat.

Before the addition of make-up butane to the effluent from the first stage the effluent must be cooled to 200° C. to prevent the cold flame reaction. The time frame before the cold flame reaction begins is 0.7–0.9 seconds.

Another method of reducing both the cold flame reaction and the flammability of the mixture entering the second reactor is by reducing the gas temperature in a partial condenser to the point where part of the MAN is condensed. Over 50% of the MAN in the effluent stream from the first reactor can be condensed by cooling the gas to 53° C. to 60° C., depending upon the pressure. This MAN can then be removed by separation from the gas stream before the gas stream is sent to the second reactor. There is a limit upon the amount of MAN which can be removed by partial condensation without condensing too much water from the gas stream and forming maleic acid. Also some of the energy removed from the gas in the partial condenser can not be recovered.

The temperature of reaction may be varied within some limits in both zones, but normally the reaction should be conducted at temperatures within a rather crucial range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in each reactor, of course, will also depend to some extent upon the size of the reactor and the $C_4$ concentration. Under usual operating conditions, in a preferred procedure, the salt bath temperature of the reactor, measured by thermocouple, is about 365° C. to about 550° C. The range of temperature preferably employed in the reactor, measured as above, should be from about 380° C. to about 515° C. and the best results are ordinarily obtained at temperatures from about 390° C. to about 430° C. Described another way, in terms of salt bath reactors with carbon steel reactor tubes about 1.0 inch in diameter, the salt bath temperature will usually be controlled between about 350° C. to about 550° C. Under normal conditions, the temperature in the reactor ordinarily should not be allowed to go above about 490° C. for extended lengths of time because of decreased yields and possible deactivation of the catalyst. The flow of salt in the circuit is maintained at a rate such that the above-specified temperature values are achieved and it has been found that the average temperature of the gases flowing through the reactor is not substantially different from the temperature of the associated salt bath except, of course, for the conventional "hot spots" which may be significantly higher, e.g. 30°–50° C. higher.

The reaction may be conducted at atmospheric, superatmospheric or below atmospheric pressure. The exit pressure will be at least slightly higher than the ambient pressure to insure a positive flow from the reaction. The pressure of the inlet gases must be sufficiently high to overcome the pressure drop through the first stage reactor and preferably through the second stage reactor without any additional compression being necessary between the two stages.

The oxidation of the n-$C_4$ hydrocarbon to maleic anhydride may be accomplished by contacting n-butane in low concentrations in oxygen with an appropriate catalyst. Air is entirely satisfactory as a source of oxygen, but synthetic mixtures of oxygen and diluent gases, such as nitrogen, also may be employed. Air enriched with oxygen may be employed.

The flow rate of the gaseous stream through the reactor may be varied within rather wide limits but a preferred range of operations is at the rate of about 25 to 300 grams of $C_4$ per liter of catalyst per hour and more preferably about 50 to about 200 grams of $C_4$ per liter of catalyst per hour. Residence times of the gas stream in the catalyst bed will normally be less than about 4 seconds, more preferably less than about one second, and down to a rate where less efficient operations are obtained. The flow rates and residence times are calculated at standard conditions of 760 mm of mercury and at 25° C. In the present invention a preferred feed for conversion to maleic anhydride is a n-$C_4$ hydrocarbon comprising a predominant amount of n-butane and more preferably at least 90 mole percent n-butane.

The Reactors

A variety of reactors will be found to be useful and multiple tube heat exchanger type reactors are quite satisfactory. The tubes of such reactors may vary in diameter from about ¼ inch to about 3 inches, and the length may be varied from about 3 to about 20 or more feet.

The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-sodium nitrite-potassium nitrite eutectic mixture. As will be recognized by one skilled in the art, the heat exchange medium may be kept at the proper temperature by heat exchangers and the like. The reactor or reaction tubes may be iron, stainless steel, carbon-steel, nickel, glass tubes such as Vycor and the like. Carbon-steel, stainless steel and nickel tubes have excellent long life under the conditions for the reactions described herein. Normally, the reactors contain a preheat zone of an inert material such as ¼ inch Alundum pellets, inert ceramic balls, nickel balls or chips and the like, present at about one-half to one-fortieth the volume of the active catalyst present.

After the gas exits the first reactor it needs to be cooled quickly. In one embodiment the cooling is continued to around 50° C. where a portion of the MAN product is condensed. However, this embodiment has a slight disadvantage due to the loss of some energy from the system. In another embodiment water can be added prior to the cooling and thereby aid in reaching the 200° C. preferred temperature and as discussed below, serves a further function in the second stage reactor. Water addition is not preferred if a partial condenser is to be used to further cool the stream for MAN removal.

After the effluent gas is cooled to the preferred 50°-200° C. range, make-up butane can be added. Very complete and thorough admixture of the added butane with the cooled effluent is required, for example by sparging the butane in a first mixer followed by a second stage mixing in a static mixer, e.g. disc and doughnut. Both mixers should be located very close to the inlet to second reactor, to avoid further cooling and to transmit the now potentially hazardous, high butane-enriched stream to the second stage reactor and the contact with the catalyst. As an extra precaution the inlet head on the second stage reactor can have a very shallow configuration.

It has been observed that the temperature of the hot spot in the second reactor is higher than in the first reactor. This result is to be attributed to the presence of maleic anhydride in the feed.

In accordance with one embodiment of the invention, the first and/or second reactor may be provided with two independent salt circuits axially spaced along the reactor tubes so that two or more different temperature zones may be provided in the reactor e.g., a first temperature zone extending from the inlet of the reactor to any desired downstream point and a second temperature zone extending from that point to the outlet of the reactor. Ordinarily, an entire reactor has a single salt circuit maintained at the operating temperature, but it may be desired to have the first temperature zone extending from the inlet of the reactor to any desired downstream point at a lower temperature than the second temperature zone extending from that point to outlet of the reactor. This temperature difference will ordinarily not exceed about 40° C. As a rule, the first and second salt baths extend over at least one-fourth of the length of the catalyst-containing tubes. The catalyst beds in the two reactors may be of substantially equal height and diameter. However, the catalyst beds of one reactor can differ in size from the catalyst beds in the other reactor so that each reactor is operated at a different space velocity.

Water may also be injected into the feed to the second stage reactor. This cools and moderates the reaction.

Generally from about 1 to 4% water may be added to the feed stream to the second stage reactor. The addition may be made prior to the gas coolers and will quench the stream to about 150° C. thereby reducing the energy required to cool the gas in the cooler. Alternatively the water and/or steam (1-2%) may be added to the second stage reactor feed at the same point as the added $C_4$. This has the advantage over feeding prior to the cooler(s) in that the steam and its energy is not lost from the system. An additional advantage is to increase the safety of the process.

The maleic anhydride may be recovered in a number of ways well known to those skilled in the art. For example, the recovery may be by direct condensation or by absorption in suitable media, with subsequent separation and purification of the maleic anhydride.

In the following examples reactors are 12 foot tubes having 1 inch outside diameter as specified below.

| length diameter | Cat. Size | ml catalyst | inert packing |
| --- | --- | --- | --- |
| 12' × 1" | 3/16" × 3/16" | 950 | ¼" Alundum pellets 12" at Bottom 6" at Top |

The reactors were encased in a 7% sodium nitrate —40% sodium nitrite —53% potassium nitrite eutectic mixture salt bath. The fist stage reactor was slowly warmed to 400° C. while passing a gas stream containing 0.5 to 0.7 mole percent n-butane and air over the catalyst beginning at about 280° C. The reactor outlet was maintained at or above about 10 psig. After the reactor had reached 400° C., the catalyst was aged by passing the n-butane/air mixture therethrough for 24 hours. The n-butane/air flow and reactor temperature were increased to obtain a desired throughput. The n-butane in the feed is increased to 1.0-1.7 mole percent and the salt bath temperature adjusted to obtain 80-90% conversion. The salt bath is operated at a maximum of 430° C. The throughput is achieved in relation to the maximum salt bath temperature and maximum hot spot of about 470° C. The hot spot is determined by a probe through the center of the catalyst bed. The temperature of the salt bath can be adjusted to achieve the desired relationship between the conversion and flow rate of the n-$C_4$/air mixture (e.g. gas hourly space velocity-GHSV). The salt temperature is adjusted to give about 85% conversion. Generally, flow rates of about 30 to 75 grams of hydrocarbon feed per hour per liter of catalyst are used.

The gas stream was cooled to about 160° C. using oil jacketed pipe coolers and the cooled gas fed to the second stage reactor. Additional vaporized n-butane was added to the exit gas from the first stage reactor increase up its n-butane concentration to 1.0–1.7 mole percent. The salt bath temperature of the second stage reactor was adjusted to give 75–85% conversion of n-butane.

The exit gas from the second stage reactor was scrubbed in a water bath to remove maleic anhydride as maleic acid in the water bath. The effluent gas from the water bath, now free of maleic anhydride, was analyzed for CO, $CO_2$, n-$C_4$, $O_2$, $N_2$ to enable calculating butane conversion, maleic anhydride selectivity and yield. The water bath was analyzed for maleic and other acid concentrations in order to close the material balance.

It is a feature of the present invention that the volume of non-condensible gases flowing from the two reactors is substantially the same as the volume of non-condensible gases which would flow from a single reactor, so that the downstream process equipment for a single reactor system will readily handle the effluent from the multiple reactor system of the present invention. The maleic anhydride condenser may be operated to condense the normal amount of maleic anhydride plus all of the additional maleic anhydride which can be produced in accordance with the process of this invention, so that the gaseous stream issuing from the condenser will contain essentially no more uncondensed maleic anhydride than the corresponding stream from a single reactor system, and thereby impose essentially no additional burden on the downstream processing equipment.

The Catalysts

The catalyst which is suitably used in forming the catalyst beds for carrying out the above-described oxidations can be any of the vanadium-phosphorus contact catalysts used in the butane oxidation art and the invention is in no way limited to any particular catalyst.

Broadly the vanadium-phosphorus-oxygen catalysts comprise vanadium, phosphorus and oxygen combined as a complex. The overall ratio of vanadium to phosphorus in the catalyst bed to be treated will have an atomic ratio of about ½ to 3 atoms of phosphorus per atom of vanadium. The vanadium-phosphorus-oxygen catalyst may also contain various stabilizers and metal additives generally in percents of less than 15 weight percent based on the total weight of vanadium and phosphorus. The atomic ratio of oxygen to the remaining components of the catalyst, when the catalyst is in the process of being used to catalyze the oxidation, is difficult to determine and is probably not constant due to the competing reactions of oxidation and reduction taking place during the reaction at high temperatures. The overall ratio of oxygen to the combined atoms of vanadium and phosphorus at room temperature would be such as about 2 to 6 atoms of oxygen per the combined atoms of vanadium and phosphorus. At any rate the catalyst is present during the reaction as an oxide of vanadium and phosphorus.

The catalytic material from which the catalyst structure is made is a vanadium-phosphorus-oxygen complex type catalyst for the conversion of hydrocarbons to the corresponding anhydride. The catalyst usually contains at least one modifying component, Me, which is a metal (including the rare earth metals), an alkali metal, an alkaline earth metal, or mixture thereof.

The precise structure of the present complex catalyst has not been determined; however, a preferred complex may be represented by formula $VP_a Me_b O_x$ wherein Me is the modifying component, a is 0.90 to 1.3, b is 0.001 or greater, preferably 0.005 to 0.4. The representation is not an empirical formula and has no significance other than representing the atom ratio of the active metal components of the catalyst. The x, in fact, has no determinate value and can vary widely, depending on the combinations within the complex. That there is oxygen present is known and the $O_x$ is representative of this.

The Me component as well as the base composition and ratios of components are all well known as described in detail in the art noted herein. The composition of the catalytic component is not the subject of the present invention although it is an integral part of the invention.

Among the various Me components which have been used either alone or in combination with each other are metal and metaloids from Group Ia, Ib, IIa, IIb, IIIa, IIIb, IVa, IVb, Va, the 4th period of VIIIb, and the rare earths of the Periodic Table of elements. Some specific Me components are Cu, Ag, Zn, Cd, Al, Ga, In, Sc, Y, La, Ge, Sn, Pb, Ti, Zr, Sb, Bi, As, Fe, Co, Ni, Ce, Pr, Nd, Cr, Li, Na, K, Rb, Fr, Nb, Te, W, Pd, Mn, Mo, Re, Sm, Hf, Ta, Th, U, Sn, B, Si, Mg, Ba, Tb and Eu.

The Me components are variously described as stabilizers, promoters, modifiers or the like. Regardless of the characterization the Me components are a part of the catalyst, in that they effect the performance thereof in the oxidation of hydrocarbons. In regard to oxidation of n-$C_4$'s some more preferred Me components are Cu, Mo, Ni, Co, Cr, Nd, Ce, Ba, Y, Sm, Te, Zr, W, Pd, Ag, Mn, Zn, Re, La, Hf, Ta, Th, U, Eu, Nb, Ru, Li, Mg, B and Si.

The catalyst may be produced with carriers or diluents. In the first stage reactor it is not preferable or desirable to dilute the actives, if the feed is normal butane, since normal butane requires a greater excitation, than for example n-butene. However in the second stage reactor it may be desirable to reduce the activity of the catalyst by adding up to 20 wt.% or more inerts to the catalyst structures. Alternatively the activity of the catalyst may be moderated by dispersing 5 to 50% (by volume) discrete inert structures, such as .alumina prepared in the same configuration as the catalyst, throughout the bed. The presence of carriers or diluents will not affect the catalyst structure. Surprisingly a spent catalyst from the first reactor may be used in the second reactor and have the desirable attributes of reduced activity with excellent selectivity.

Particularly advantageous catalysts are those described in Barone U.S. Pat. No. 4,251,390. The resultant catalyst complex is characterized as a mixed oxide, however, the structure of the complex has not been determined but may be conveniently represented by a formula such as $V P_a Zn_b Si_c Li_d O_x$ where a is 0.90 to 1.3, b is 0.005 to 0.2, c is 0 to 0.3 and d is 0 to 0.15. As noted above, this representation is not an empirical formula and has no significance other than representing the atom ratio of the components of the catalyst. Other suitable catalysts are the catalysts described in Kerr, et al U.S. Pat. No. 3,980,585 and Kerr U.S. Pat. No. 4,105,586.

The catalyst may be employed as pellets, disc, flakes, wafers, or any other convenient shape which will facilitate its use in the tubular reactors employed for this type of vapor phase reaction. For example the catalyst may be prepared as tablets having a hole or bore therethrough as disclosed in U.S. Pat. No. 4,283,307. Generally, the unsupported catalyst will have higher surface area than supported catalysts. The final catalyst particle size for this arrangement is usually about 2½ to about 10

Tyler mesh. In any event after activation the surface area is preferably less than 100 m²/g and at least 1 m²/g preferably at least 5 m²/g.

The use of this class of catalyst for the partial oxidation of $C_4$-$C_{10}$ hydrocarbons to the corresponding anhydrides is generally recognized. They have been widely considered for the conversion of normal $C_4$ hydrocarbons, both the alkane, n-butane, and alkene, n-butene, for the production of maleic anhydride, which has a wide commercial usage.

Operating in accordance with the present process parameters it is possible to increase the effective conversion of the reactors over that of a reactor operated singly. Surprisingly the yield of maleic anhydride can be increased 8-10 wt %, waste gas effluent is reduced, the power consumption per ton of MA is decreased, steam usage is decreased and capital cost is reduced.

THE EXAMPLES

The C, S and Y used in reporting reaction results have the following meaning and relationship: C(conversion)×S (selectivity)=Y (yield).

The term "weight yield" means the amount of maleic anhydride produced from a given amount of n-butane, calculated as follows:

$$\text{wt yield} = \frac{98 \text{ (mole wt of maleic anhydride)}}{58 \text{ (mole wt of butane)}} \times \text{mole \% yield}$$

Example 1

Each reactor consists of a 0.824" ID tube jacketed by circulating salt and packed with 10.5' of conditioned 3/16"×3/16" solid tablets of catalyst which contains PVO and a small amount of Zn as described in U.S. Pat. No. 4,251,390. The reactors are piped in series with appropriate temperature control of the interconnecting lines to prevent MAN condensation.

Air and butane for the first stage reactor are brought in under automatic flow control, mixed and fed to the reactor inlet. The first stage effluent gases are cooled by a temperature controlled oil jacketed pipe exchanger to 160° C. then mixed with a flow controlled quantity of make-up butane and fed to the second stage reactor.

Each reactor has its own independent salt temperature control system to maintain the target butane conversion. A travelling thermocouple inside a ⅛" thermowell runs the length of each reactor to monitor the temperature profile and determine the location and magnitude of the hot spot.

System pressure is maintained by a pressure control valve at the outlet of the second stage. The second stage effluent gas is passed through a water-containing scrubber for MAN removal and the vent gases are sent to incineration. The scrubber is drained periodically when the MAN concentration is well below the saturation point and replenished with fresh water.

Sample gases are taken at the inlet and outlet of each stage, conditioned by scrubbing for MAN and light acids removal and drying over calcium chloride and passed through on-line infrared analyzers for butane, CO and $CO_2$ analysis.

Runs have been made at a variety of conditions and results for several of the key runs are shown in TABLE 1. The overall results are expressed in terms of MAN weight yield, which is a measure of process efficiency and productivity and pounds MAN/hr/total cu ft of catalyst, which is a measure of production capacity.

The laboratory experiments were conducted by fixing the inlet pressure to the first reactor at 29 psig and the second reactor at 20 psig. The power savings per unit of MAN production according to the present invention is calculated to be about 30% compared to both reactors operating in parallel at 20 psig inlet pressure. In commercial installations this savings can be up to 50% when the two reactors are optimized with respect to operating pressure.

The catalysts used in these runs were conditioned separately using standard procedures and have under 1200 hours on-stream. Their performance as single stage reactors is summarized below:

| Stage | 1 | 2 |
|---|---|---|
| Run | 2-B | 2-D |
| C4 in, vol % | 1.65 | 1.66 |
| Salt Temp., C | 397 | 403 |
| Hot Spot, C | 423 | 426 |
| Conv, % | 82.4 | 80.6 |
| Sel, mole % | 67.1 | 65.7 |
| MAN wt Yield, % | 93.4 | 90.6 |

In TABLE 1

$$\text{Overall Conversion} = \frac{(a + b) - c}{(a + b)} \times 100$$

where
a = mole % Butane In Feed To first stage reactor
b = mole % Butane in Feed to second stage reactor
c = mole % Butane in effluent from second stage reactor

TABLE 1

SERIES BED PILOT PLANT RUNS

RUN CONDITIONS REACTOR ID = 0.824"
INLET PRESSURE OF SECOND BED = 20 PSIG (CONTROL POINT)
INLET PRESSURE OF FIRST BED = 26 PSIG WHEN OPERATED IN SERIES
BED HEIGHTS = 10.5' (BOTH BEDS)
GHSV = 2500 Hr (BOTH BEDS)

| RUN | 2-A | 2-B | 2-C | 2-D | 2-E | 2-F | 2-G | 2-H | 2-I | 2-J | 2-K | 2-L |
|---|---|---|---|---|---|---|---|---|---|---|---|---|
| FIRST BED | | | | | | | | | | | | |
| C4 IN, Mole % | 1.64 | 1.65 | 1.64 | SHUT DOWN | 1.65 | 1.66 | 1.65 | 1.39 | 1.66 | 1.65 | 1.41 | 1.66 |
| SALT T, °C. | 397 | 397 | 379 | | 393 | 394 | 392 | 391 | 377 | 376 | 389 | 392 |
| HOT SPOT T, °C. | 419 | 423 | 397 | | 419 | 422 | 416 | 410 | 391 | 391 | 409 | 420 |
| DELTA HOT SPOT, °C. | 22 | 26 | 18 | | 26 | 28 | 24 | 19 | 14 | 15 | 20 | 28 |
| CO/CO2 RATIO | 1.35 | 1.31 | 1.32 | | 1.27 | 1.26 | 1.27 | 1.26 | 1.48 | 1.34 | 1.28 | 1.26 |
| CONV, % | 75.4 | 82.4 | 65.3 | | 80.8 | 82.2 | 79.9 | 79.8 | 65.4 | 64.9 | 80.4 | 82.2 |
| SEL, M % | 70.8 | 67.1 | 75 | | 69.4 | 68.5 | 69.4 | 69.3 | 75.3 | 76.1 | 69.8 | 68.6 |
| MAN WT YIELD, % | 90.2 | 93.4 | 82.7 | | 94.7 | 95.1 | 93.7 | 93.4 | 83.2 | 83.4 | 94.8 | 94.9 |

TABLE 1-continued

SERIES BED PILOT PLANT RUNS

RUN CONDITIONS REACTOR ID = 0.824"
INLET PRESSURE OF SECOND BED = 20 PSIG (CONTROL POINT)
INLET PRESSURE OF FIRST BED = 26 PSIG WHEN OPERATED IN SERIES
BED HEIGHTS = 10.5' (BOTH BEDS)
GHSV = 2500 Hr (BOTH BEDS)

| RUN | 2-A | 2-B | 2-C | 2-D | 2-E | 2-F | 2-G | 2-H | 2-I | 2-J | 2-K | 2-L |
|---|---|---|---|---|---|---|---|---|---|---|---|---|
| SECOND BED | | | | | | | | | | | | |
| $C_4$ IN, Mole % | SHUT DOWN | 1.51 | 1.49 | 1.66 | 1.49 | 1.51 | 1.51 | 1.46 | 1.51 | 1.51 | 1.51 | 1.36 |
| SALT T, °C. | | 411 | 405 | 403 | 417 | 410 | 415 | 408 | 406 | 410 | 407 | 410 |
| HOT SPOT T, °C. | | 450 | 450 | 426 | 465 | 450 | 464 | 451 | 450 | 465 | 450 | 448 |
| DELTA HOT SPOT, °C. | | 39 | 45 | 23 | 48 | 40 | 49 | 43 | 44 | 55 | 43 | 38 |
| $CO/CO_2$ RATIO | | 1.19 | 1.13 | 1.31 | 1.16 | 1.15 | 1.14 | 1.14 | 1.15 | 1.12 | 1.12 | 1.36 |
| CONV, % | | 75.3 | 75.5 | 80.6 | 79.4 | 712.5 | 78.3 | 77.0 | 74.4 | 80.4 | 75.5 | 76.7 |
| SEL, M % | | 59.6 | 60.8 | 65.7 | 56 | 61.7 | 57 | 60.8 | 62.3 | 57.1 | 62.6 | 58.6 |
| MAN WT YIELD, % | | 76.8 | 78.6 | 90.6 | 76.2 | 76.6 | 76.5 | 80.1 | 79.3 | 78.7 | 80.9 | 76.9 |
| OVERALL | | | | | | | | | | | | |
| CONV % | 75.4 | 78.4 | 86.1 | 80.6 | 89.2 | 86.1 | 88.5 | 86.9 | 85.3 | 88.7 | 86.2 | 88.7 |
| MAN WT. YIELD % | 90.2 | 94.8 | 98.2 | 87.2 | 94.2 | 94.8 | 94.0 | 94.5 | 98.7 | 98.8 | 95.5 | 95.1 |
| PRODUCTIVITY, LB/H/CU FT CAT. | 6.3 | 5.6 | 5.3 | 6.4 | 5.6 | 5.7 | 5.6 | 5.1 | 5.4 | 5.3 | 5.3 | 5.4 |
| POWER | | | | | | | | | | | | |
| POWER FACTOR | 0.99[1] | 0.68 | 0.71 | 1.01[1] | 0.67 | 0.65 | 0.67 | 0.73 | 0.7 | 0.7 | 0.7 | 0.7 |
| POWER SAVINGS, %[2] | — | 32 | 29 | — | 33 | 35 | 33 | 27 | 30 | 30 | 30 | 30 |

NOTES:
[1]UNITY POWER FACTOR WHEN ONLY ONE REACTOR OPERATING = POWER PER UNIT OF MALIC ANHYDRIDE PRODUCTION
[2]% SAVINGS IN POWER PER UNIT OF MALIC ANHYDRIDE PRODUCTION WHEN TWO REACTORS ARE IN OPERATION IN SERIES

The invention claimed is:

1. A process for the partial oxidation of butane to form maleic anhydride comprising bringing a mixture of vaporized butane and air of controlled butane content into the presence of a contact vanadium-phosphorus-oxygen catalyst in a first oxidation zone under controlled pressure and temperature conditions, cooling the gaseous effluent from the first oxidation zone to a temperature in the range of 50° to 200° C. which is below the cold flame temperature of butane at the pressure at the outlet of the first oxidation zone, introducing a controlled amount of butane into the cooled gaseous effluent from the first oxidation zone, introducing said cooled butane enriched stream into the second oxidation zone, and bringing the thus butane-enriched mixture into contact with a vanadium-phosphorus-oxygen catalyst disposed in the second zone under controlled pressure and temperature.

2. The process according to claim 1 wherein the mixture entering the first oxidation zone contains 1 to 2 mole % butane.

3. The process according to claim 1 wherein the mixture entering the second oxidation zone contains 1.0 to 1.8 mole % butane.

4. The process according to claim 1 wherein the temperature in each zone is in the range of 380°–515° C.

5. The process according to claim 1 wherein water is introduced into the gaseous effluent from the first oxidizing zone.

6. The process according to claim 1 wherein the butane introduced into said gaseous effluent is thoroughly mixed into said effluent and rapidly brought into contact with the catalyst in the second zone.

7. The process according to claim 1 wherein no additional oxygen is introduced into the gaseous effluent stream.

8. The process according to claim 4 wherein the temperature in each zone is independently maintained.

9. The process according to claim 4 wherein the second zone is maintained at two different temperatures.

10. The process according to claim 8 wherein the second zone is maintained at two different temperatures.

11. The process according to claim 8 wherein the first zone is maintained at two different temperatures.

12. The process according to claim 8 wherein both the first and second zones are maintained at two different temperatures.

13. The process according to claim 5 wherein said water is introduced before said cooling.

14. The process according to claim 5 wherein said water is introduced after said cooling.

15. The process according to claim 1 wherein a portion of a maleic anhydride product is condensed and removed from the gaseous effluent before introducing said butane.

16. The process according to claim 13 wherein said water quenches the gaseous effluent.

17. The process according to claim 13 wherein from about 1 to 4% water is introduced.

18. The process according to claim 14 wherein from about 1 to 2% water is introduced.

19. The process according to claim 18 wherein the water is introduced concurrently with the butane into the cooled gaseous effluent.

20. The process according to claim 18 wherein said water comprises steam.

21. A process for the partial oxidation of butane to form maleic anhydride comprising bringing a mixture of vaporized butane and air having 1.0 to 2.0 mole % butane content into the presence of a contact vanadium-phosphorus-oxygen catalyst in a first oxidation zone under controlled pressure and temperature conditions, cooling the gaseous effluent comprising maleic anhydride, unreacted butane and oxygen from the first oxidation zone to a temperature in the range of 50° to about 200° C., introducing a controlled amount of butane into the cooled gaseous effluent from the first oxidation zone to provide up to 1.8 mole % butane, introducing said cooled, butane-enriched stream and oxygen, said oxygen being characterized as being only the oxygen from the first oxidation zone, into the second oxidation zone under controlled pressure and temperature, and bringing the thus butane-enriched mixture into contact with a vanadium-phosphorus-oxygen catalyst disposed in the second zone.

22. A process for the partial oxidation of butane to form maleic anhydride comprising bringing a mixture of vaporized butane and air of controlled butane content into the presence of a contact vanadium-phosphorus-oxygen catalyst in a first oxidation zone under controlled pressure and temperature conditions, cooling the gaseous effluent comprising maleic anhydride from the first oxidation zone to a temperature in the range of 50° to 60° C., by condensing and removing a portion of said maleic anhydride from said effluent, introducing a controlled amount of butane into the cooled gaseous effluent from the first oxidation zone, introducing said cooled butane enriched stream into the second oxidation zone, and bringing the thus butane-enriched mixture into contact with a vanadium-phosphorus-oxygen catalyst disposed in the second zone under controlled pressure and temperature.

23. A process for the partial oxidation of butane to form maleic anhydride comprising bringing a mixture of vaporized butane and air having 1.0 to 2.0 mole % butane content into the presence of a contact vanadium-phosphorus-oxygen catalyst in a first oxidation zone under controlled pressure and temperature conditions, cooling the gaseous effluent comprising maleic anhydride, unreacted butane and oxygen from the first oxidation zone to a temperature in the range of 50 to about 200° C. which is below the cold flame temperature of butane at the pressure at the outlet of the first oxidation zone, introducing a controlled amount of butane to provide up to 1.8 mole % butane and from 1 to 2% water into the cooled gaseous effluent from the first oxidation zone, introducing said cooled, butane-enriched stream and oxygen, said oxygen being characterized as being only the oxygen from the first oxidation zone, into the second oxidation zone under controlled pressure and temperature, and bringing the thus butane-enriched mixture into contact with a vanadium-phosphorus-oxygen catalyst disposed in the second zone.

24. A process for the partial oxidation of butane to form maleic anhydride comprising bringing a mixture of vaporized butane and air having 1.0 to 2.0 mole % butane content into the presence of a contact vanadium-phosphorus-oxygen catalyst in a first oxidation zone under controlled pressure and temperature conditions, introducing from 1 to 4% water into the gaseous effluent comprising maleic anhydride, unreacted butane and oxygen from the first oxidation zone, cooling said water containing effluent to a temperature in the range of 50° to about 200° C. which is below the cold flame temperature of butane at the pressure at the outlet of the first oxidation zone, introducing a controlled amount of butane and into the cooled gaseous effluent from the first oxidation zone to provide up to 1.8 mole % butane, introducing said cooled, butane-enriched stream and oxygen, said oxygen being characterized as being only the oxygen from the first oxidation zone, into the second oxidation zone under controlled pressure and temperature, and bringing the thus butane-enriched mixture into contact with a vanadium-phosphorus-oxygen catalyst disposed in the second zone.

25. The process according to claim 24 wherein said water quenches the gaseous effluent.

26. A process for the partial oxidation of butane to form maleic anhydride comprising the steps of:
(a) bringing a mixture of vaporized butane and air having a controlled butane content of between 1 to 2 mol % into the presence of a contact vanadium-phosphorus-oxygen catalyst in a first oxidation zone under controlled pressure and temperature conditions;
(b) cooling the gaseous effluent from the first oxidation zone to a temperature in the range of 50° to about 200° C. which is below the cold flame temperature of butane at the pressure at the outlet of the first oxidation zone;
(c) introducing a controlled amount of butane to provide up to 1.8 mol % butane in the cooled gaseous effluent from the first oxidation zone;
(d) introducing the cooled butane enriched stream into a second oxidation zone; and
(e) bringing the butane-enriched mixture into contact with a vanadium-phosphorus-oxygen catalyst disposed in the second oxidation zone under controlled pressure and temperature.

* * * * *